(12) United States Patent
Kraft et al.

(10) Patent No.: US 11,001,941 B2
(45) Date of Patent: May 11, 2021

(54) POLYSACCHARIDE FIBERS AND METHOD FOR PRODUCING SAME

(71) Applicant: NUTRITION & BIOSCIENCES USA 4, INC., Rochester, NY (US)

(72) Inventors: Gregor Kraft, Timelkam (AT); Gert Kroner, Seewalchen (AT); Thomas Röder, Vöcklabruck (AT); Heinrich Firgo, Vöcklabruck (AT)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

(21) Appl. No.: 16/038,471

(22) Filed: Jul. 18, 2018

(65) Prior Publication Data
US 2018/0320291 A1    Nov. 8, 2018

Related U.S. Application Data

(62) Division of application No. 14/899,225, filed as application No. PCT/AT2014/000122 on Jun. 13, 2014, now Pat. No. 10,196,758.

(30) Foreign Application Priority Data

Jun. 18, 2013    (AT) .................. A 490/2013

(51) Int. Cl.
| | | |
|---|---|---|
| *D21F 13/08* | (2006.01) | |
| *D04H 1/28* | (2012.01) | |
| *D04H 3/013* | (2012.01) | |
| *D04H 1/4258* | (2012.01) | |
| *D01D 5/06* | (2006.01) | |
| *D01F 2/02* | (2006.01) | |
| *C08B 37/00* | (2006.01) | |
| *B29C 48/05* | (2019.01) | |
| *B29C 48/00* | (2019.01) | |
| *B29C 48/14* | (2019.01) | |
| *D01F 9/00* | (2006.01) | |
| *D21H 13/02* | (2006.01) | |
| *D21H 13/08* | (2006.01) | |
| *A61L 15/28* | (2006.01) | |
| *D01F 2/24* | (2006.01) | |
| *B29L 31/00* | (2006.01) | |

(52) U.S. Cl.
CPC ............... *D01D 5/06* (2013.01); *A61L 15/28* (2013.01); *B29C 48/022* (2019.02); *B29C 48/05* (2019.02); *B29C 48/147* (2019.02); *C08B 37/0009* (2013.01); *D01F 2/02* (2013.01); *D01F 2/24* (2013.01); *D01F 9/00* (2013.01); *D04H 1/28* (2013.01); *D04H 1/4258* (2013.01); *D04H 3/013* (2013.01); *D21H 13/02* (2013.01); *D21H 13/08* (2013.01); *B29K 2005/00* (2013.01); *B29L 2031/731* (2013.01)

(58) Field of Classification Search
CPC .......... D21H 13/02; D21H 13/08; D01F 2/02; D01F 2/06; D01F 2/08; C08L 1/02; C08L 1/24; C08L 5/02; C08B 37/0009; C08B 37/0021; D01D 5/06; D04H 1/28; D04H 1/3013; D04H 1/425; D04H 1/4258
USPC ....... 162/157.7; 264/188, 189, 178 F, 178 R, 264/205, 207; 536/123.1, 123.12
See application file for complete search history.

(56) References Cited

U.S. PATENT DOCUMENTS

| | | | | |
|---|---|---|---|---|
| 6,846,924 B1 * | 1/2005 | Malmgren | ................ | D01F 2/28 536/102 |
| 7,000,000 B1 * | 2/2006 | O'Brien | .................. | C12P 19/08 536/123.12 |
| 2013/0313737 A1 * | 11/2013 | O'Brien | .................... | D01F 9/00 264/13 |

* cited by examiner

*Primary Examiner* — Eric Hug

(57) ABSTRACT

The present invention relates to a direct dissolving process for the production of polysaccharide fibers which contain α(1→3)-glucan as a fiber-forming substance, with aqueous sodium hydroxide solution as a solvent, as well as to the fibers made thereby, and to their use.

6 Claims, No Drawings

POLYSACCHARIDE FIBERS AND METHOD FOR PRODUCING SAME

The present application is a division of U.S. patent application Ser. No. 14/899,225, filed Dec. 17, 2015 and published as US 2016-0177471 A1, which is a national-stage entry under 35 U.S.C. § 371 of International Patent Application No. PCT/AT2014/000122, filed Jun. 13, 2014 and published as WO 2014/201481, which claims priority to Austrian Patent Application No. A 490-2013, filed Jun. 18, 2013, the entire disclosure of each of which is hereby incorporated by reference herein.

FIELD OF THE INVENTION

The present invention relates to a direct dissolving process for the production of polysaccharide fibers which contain α(1→3)-glucan as a fiber-forming substance, with aqueous sodium hydroxide solution as a solvent, as well as to the fibers made thereby, and to their use.

BACKGROUND OF THE INVENTION

Polysaccharides are becoming increasingly important, as they are materials that can be obtained from renewable raw materials. One of the most frequently occurring polysaccharides is cellulose. Cotton fibers, which consist almost exclusively of cellulose, are an example of the significance of polysaccharides. However, also materials obtained from other cellulosic raw materials, e.g., cellulosic synthetic fibers, are continuing to gain in importance.

The generic names "viscose fibers" and "modal fibers" were assigned by BISFA (the International Bureau for the Standardization of Man-made Fibers) to cellulose fibers produced through chemical derivatization of cellullose with the help of aqueous sodium hydroxide solution and carbon disulfide ($CS_2$).

The name "modal fiber" is a generic term which, as defined by BISFA, stands for a cellulose fiber having a defined high wet strength and an equally defined high wet modulus (i.e., the force required to produce an elongation of the fiber of 5% in its wet state).

However, to date, only one method for the large-scale production of fibers of the viscose and modal types has gained acceptance, namely, the viscose process and variations thereof.

From many patent specifications and other publications, it has generally been known to those skilled in the art for quite some time how this method is carried out. A method for the production of modal fibers is, for example, known from AT 287.905 B.

The big downside of all viscose processes is the use of $CS_2$ that must be recovered with great effort.

The generic name "lyocell fibers" was assigned by BISFA to cellulose fibers produced from solutions in an organic solvent without the formation of a derivative.

However, to date, only one method for the large-scale production of fibers of the lyocell type has gained acceptance, namely, the amine-oxide process. In this method, a tertiary amine oxide, preferably N-methylmorpholine-N-oxide (NMMO), is used as the solvent.

Tertiary amine oxides have long been known as alternative solvents for cellulose. It is known from U.S. Pat. No. 2,179,181, for example, that tertiary amine oxides are capable of dissolving pulp without derivatization and that cellulosic molded bodies, e.g., fibers, can be made from these solutions. U.S. Pat. No. 3,447,939 describes cyclic amine oxides used as solvents for cellulose.

From numerous patent specifications and other publications, it has been known to those skilled in the art for quite some time how this method is carried out. EP 356 419 B1, for example, describes how the solution is prepared, and EP 584 318 B1 describes how such solutions of cellulose in aqueous tertiary amine oxides are spun.

Being a direct dissolving process, the lyocell process is significantly safer from an ecological perspective than the viscose processes, however, it comes with disadvantages in terms of process engineering, as, due to the economic necessity of providing nearly completely closed process cycles, substances may accumulate in the cycles.

US 7,000,000 describes fibers obtained by spinning a solution of polysaccharides which substantially consist of repeating hexose units linked via α(1→3)-glycosidic bonds. These polysaccharides can be produced by bringing an aqueous solution of saccharose into contact with glucosyltransferase (GtfJ), isolated from *Streptococcus salivarius* (Simpson et al., Microbiology, vol. 41, pp 1451-1460 (1995)). As used in this context, "substantially" means that within the polysaccharide chains there may exist occasional defective locations where other bond configurations may occur. For the purposes of the present invention, these polysaccharides shall be referred to as "α(1→3)-glucan".

US 7,000,000 first discloses possibilities for the enzymatic production of α(1→3)-glucan from monosaccharides. In this way, relatively short-chained polysaccharides can be produced without the loss of monomer units, as the polymer chains are built from the monomer units. Contrary to the production of short-chained cellulose molecules, the production of α(1→3)-glucan keeps getting less expensive the shorter the polymer chains are, as in that case the required residence time in the reactors will be short.

According to US 7,000,000, the α(1→3)-glucan is to be derivatized, preferably acetylated. Preferably, the solvent is an organic acid, an organic halogen compound, a fluorinated alcohol, or a mixture of such components. These solvents are costly and complex to regenerate.

However, studies have also shown that α(1→3)-glucans dissolve in diluted aqueous sodium hydroxide solution.

Object

In view of such prior art, the object was therefore to provide an alternative direct dissolving process for the production of polysaccharide fibers, which makes do without the $CS_2$ needed in the viscose process and without the effort-consuming closure of cycles of a lyocell process.

DESCRIPTION OF THE INVENTION

The above described object is solved by a new direct dissolving process for the production of a polysaccharide fiber whose fiber-forming substance is α(1→3)-glucan, the direct dissolving process being based on aqueous sodium hydroxide solution.

Hence, the subject-matter of the present invention is, on the one hand, a method for the production of a polysaccharide fiber whose fiber-forming substance is α(1→3)-glucan, the method being a direct dissolving process and the solvent being aqueous sodium hydroxide solution.

Surprisingly, it was found that standard spin baths as used in the viscose process (they contain about 100 g/l $H_2SO_4$ and about 250 g/l $Na_2SO_4$) yield very poor results, but that two other, very different spin bath compositions yield significantly better results.

1. High-acid spinning: it was discovered that filament formation and the stretchability of the regenerated filament improve significantly when increasing the concentration of sulfuric acid in the spin bath. The examined range with good spinning characteristics reaches from 200 to 500 grams of sulfuric acid per liter of spin bath.

2. Low-acid spinning: the second spinning range, which exhibited a significantly better spinning reliability, is at very low acid concentrations below 60 grams per liter of spin bath, preferably from 20-60 g/l. Good results were also obtained using a two-bath system, where the first bath has very high salt contents and a very low acid concentration, whereby the spun filament is only coagulated at first and is regenerated only in the second, acid regeneration bath.

In a preferred embodiment of the inventive method, the $H_2SO_4$ concentration in the spin bath is therefore between 200 and 500 g/l.

In a second preferred embodiment of the inventive method, the $H_2SO_4$ concentration in the spin bath is therefore between 20 and 60 g/l.

In a preferred embodiment of the inventive method, the spun fiber is subsequently stretched in an acid regeneration bath.

According to the invention, the NaOH concentration in the spinning solution is to be between 4.0 and 5.5% by weight, related to the total quantity of the spinning solution. Outside this range, the solubility of the glucan is not sufficiently ensured.

For the purposes of the present invention, the term "fiber" shall comprise both staple fibers having a defined staple length and continuous filaments. All principles of the invention that are described hereinafter generally apply to both staple fibers and continuous filaments.

The single fiber titer of the inventive fibers can be between 0.1 and 10 dtex. Preferably, it is between 0.5 and 6.5 dtex, and more preferably between 0.9 and 6.0 dtex. In the case of staple fibers, the staple length is usually between 0.5 and 120 mm, preferably between 20 and 70 mm, and more preferably between 35 and 60 mm. In the case of continuous filaments, the number of individual filaments in the filament yarn is between 50 and 10,000, preferably between 50 and 3,000.

The $\alpha(1\rightarrow3)$-glucan can be prepared by bringing an aqueous solution of saccharose into contact with glucosyl-transferase (GtfJ) isolated from *Streptococcus salivarius* (Simpson et al., Microbiology, vol. 41, pp 1451-1460 (1995)).

In a preferred embodiment of the method according to the invention, at least 90% of the $\alpha(1\rightarrow3)$-glucan are hexose units and at least 50% of the hexose units are linked via $\alpha(1\rightarrow3)$-glycosidic bonds.

The method for the production of the inventive fiber consists of the following steps:

1. Preparing an $\alpha(1\rightarrow3)$-glucan solution in diluted aqueous sodium hydroxide solution.
2. Extruding the $\alpha(1\rightarrow3)$-glucan-containing spinning solution through a spinneret into a sulfuric acid spin bath, stretching the fibers in an acid regeneration bath, and post-treatment.

The concentration of the fiber-forming substance in the spinning solution can be between 4 and 18% by weight, preferably it is between 4.5 and 12% by weight.

The degree of polymerization of the $\alpha(1\rightarrow3)$ glucan employed in the method according to the invention, expressed as weight average $DP_w$, can be between 200 and 2000; values between 500 and 1000 are preferred.

In a preferred embodiment at least 90% of the $\alpha(1\rightarrow3)$-glucan of the polysaccharide fiber according to the invention are hexose units and at least 50% of the hexose units are linked via $\alpha(1\rightarrow3)$-glycosidic bonds.

The above described polysaccharide fiber whose fiber-forming substance is $\alpha(1\rightarrow3)$-glucan and which was produced using the also above described direct dissolving process in aqueous sodium hydroxide solution is also the subject-matter of the present invention.

The use of the inventive fibers for the production of textile products such as yarns, woven fabrics, or knitted fabrics as well as of various dry-laid and wet-laid papers, nonwovens, hygiene articles such as tampons, panty liners, and diapers, and of other nonwovens, especially absorbent nonwoven products, is also the subject-matter of the present invention.

The invention will be described below with reference to examples. However, the invention is not expressly limited to these examples but also includes all other embodiments that are based on the same inventive concept.

EXAMPLES

The degree of polymerization of the $\alpha(1\rightarrow3)$-glucans was determined by means of GPC in DMAc/LiCl. Subsequently, it is always the weight average of the degree of polymerization ($DP_w$) that is specified.

Example 1

An aqueous glucan solution containing 9% of $\alpha(1\rightarrow3)$-glucan with a $DP_W$ of 800 as well as 4.5% by weight of NaOH was cooled down to 3° C., filtered, and deaerated. By using a spinneret, the solution was extruded into a spin bath at 35° C., containing 300 g/l of sulfuric acid, and 50 g/l of sodium sulfate. The spinneret had 53 perforations with a diameter of 50 μm. In order to achieve adequate fiber strength, stretching in the regeneration bath (97° C., 25 g/l $H_2SO_4$) was carried out. The draw-off velocity was 30 m/min.

The properties of the obtained fibers are listed in Table 1.

Example 2

An aqueous glucan solution containing 9% of $\alpha(1\rightarrow3)$-glucan with a $DP_W$ of 1000 as well as 4.8% by weight of NaOH was cooled down to 0° C., filtered, and deaerated. By using a spinneret, the solution was extruded into a spin bath at 20° C., containing 35 g/l of sulfuric acid, 280 g/l of sodium sulfate, and 45 g/l of zinc sulfate. The spinneret had 53 perforations with a diameter of 40 μm. In order to achieve adequate fiber strength, stretching in the regeneration bath (92° C., 55 g/l $H_2SO_4$) was carried out. The draw-off velocity was 25 m/min. The properties of the obtained fibers are listed in Table 1.

TABLE 1

| example | titer dtex | FFk cN/tex | FDk % |
|---|---|---|---|
| ex. 1 | 1.7 | 15.3 | 11.1 |
| ex. 2 | 1.7 | 19.1 | 9.2 |

FFk fiber strength, conditioned
FDk fiber elongation, conditioned

What is claimed is:

1. A non-woven product comprising a polysaccharide fiber whose fiber-forming substance is $\alpha(1\rightarrow3)$-glucan, wherein the α(1→3)-glucan has a weight average degree of polymerization between 200 and 2000.

2. The non-woven product of claim 1, wherein at least 90% of the α(1→3)-glucan are hexose units and at least 50% of the hexose units are linked via α(1→3)-glycosidic bonds.

3. The non-woven product of claim 1 or 2, wherein the polysaccharide fiber is a continuous filament.

4. The non-woven product of claim 1 or 2, wherein the polysaccharide fiber is a staple fiber.

5. The non-woven product of claim 1 or 2, wherein said fiber is produced using a direct dissolving process in aqueous sodium hydroxide solution.

6. The non-woven product of claim 1 or 2, wherein the weight average degree of polymerization is between 500 and 1000.

\* \* \* \* \*